(12) United States Patent
S et al.

(10) Patent No.: US 9,207,214 B2
(45) Date of Patent: Dec. 8, 2015

(54) AUTO BEAM OPTIMIZATION FOR PHASED ARRAY WELD INSPECTION

(71) Applicant: General Electric Company, Schenectady, NY (US)

(72) Inventors: Anandamurugan S, Bangalore (IN); Sangeetha Mylswamy, Tamilnadu (IN)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 339 days.

(21) Appl. No.: 13/873,374

(22) Filed: Apr. 30, 2013

(65) Prior Publication Data
US 2014/0318249 A1    Oct. 30, 2014

(51) Int. Cl.
*G01N 29/04* (2006.01)
*B23K 31/12* (2006.01)
*G01N 29/24* (2006.01)
*G01N 29/26* (2006.01)

(52) U.S. Cl.
CPC .............. *G01N 29/04* (2013.01); *B23K 31/125* (2013.01); *G01N 29/2487* (2013.01); *G01N 29/262* (2013.01); *G01N 2291/056* (2013.01); *G01N 2291/106* (2013.01); *G01N 2291/2675* (2013.01)

(58) Field of Classification Search
CPC .............. G01N 29/04; G01N 29/2487; G01N 2291/2675; G01N 2291/106; G01N 29/262; B23K 31/125
USPC ............................................ 73/588, 599, 602
See application file for complete search history.

(56) References Cited

U.S. PATENT DOCUMENTS

| | | | |
|---|---|---|---|
| 6,405,596 B1 | 6/2002 | Kruzic | |
| 7,168,322 B2 * | 1/2007 | Bardoux et al. | 73/588 |
| 7,966,860 B2 * | 6/2011 | Dijkstra | 73/1.86 |

(Continued)

FOREIGN PATENT DOCUMENTS

WO    0171338 A1    9/2001

OTHER PUBLICATIONS

Chen et al., "The Design of an Ultrasonic Phased Array System on Pipelines Weld Inspection", Proceedings of the 5th Biennial, International Pipeline Conference: Presented at the International Conference(IPC 2004), Calgary, Alberta, Canada, Oct. 4-8, 2004, ASME, New York, US, vol. 2, No. IPC04-0719, Oct. 4, 2004, pp. 905-908.

(Continued)

*Primary Examiner* — J M Saint Surin
(74) *Attorney, Agent, or Firm* — Cooper Legal Group, LLC

(57) ABSTRACT

A method of computing optimal beam numbers of a phased-array ultrasonic weld inspection arrangement. The arrangement is for inspecting a weld that is within an area of interest that has a known dimension and with the inspection arrangement being at a known offset distance from the weld. The selection is such that operation of the at least one element provides sufficient information data for weld analysis. The elements extend along an ultrasonic transmission wedge of the arrangement that supports the extent of the elements at a wedge angle relative to the welded material. The method includes utilizing the dimension of the weld area of interest and dimension of offset of the inspection arrangement from the weld within calculation that yields the selection of the at least one element.

10 Claims, 7 Drawing Sheets

(56) References Cited

U.S. PATENT DOCUMENTS

| | | | |
|---|---|---|---|
| 2008/0190205 A1* | 8/2008 | Messer et al. | 73/592 |
| 2008/0289425 A1 | 11/2008 | Dijkstra et al. | |
| 2009/0199642 A1* | 8/2009 | Fukutomi et al. | 73/598 |
| 2009/0320601 A1* | 12/2009 | Kleinert | 73/628 |
| 2010/0101326 A1 | 4/2010 | Iizuka et al. | |
| 2011/0296923 A1 | 12/2011 | Cataldo et al. | |
| 2013/0047729 A1 | 2/2013 | Wigh et al. | |
| 2013/0218490 A1* | 8/2013 | Poirier et al. | 702/56 |

OTHER PUBLICATIONS

Moles et al. "Pipeline girth Weld Inspections Using Ultrasonic Phased Arrays", American Society of Mechanical Engineers, Pressure Vessels and Piping Division(Publication) PVP—Ultrasonic Nondestructive Evaluation for Materials Science and Industries 2003, American Society of Me, vol. 456, Jun. 2, 2003, pp. 1-15.

PCT Search Report and Written Opinion issued in connection with corresponding Application No. PCT/US2014/035416 on Aug. 11, 2014.

* cited by examiner

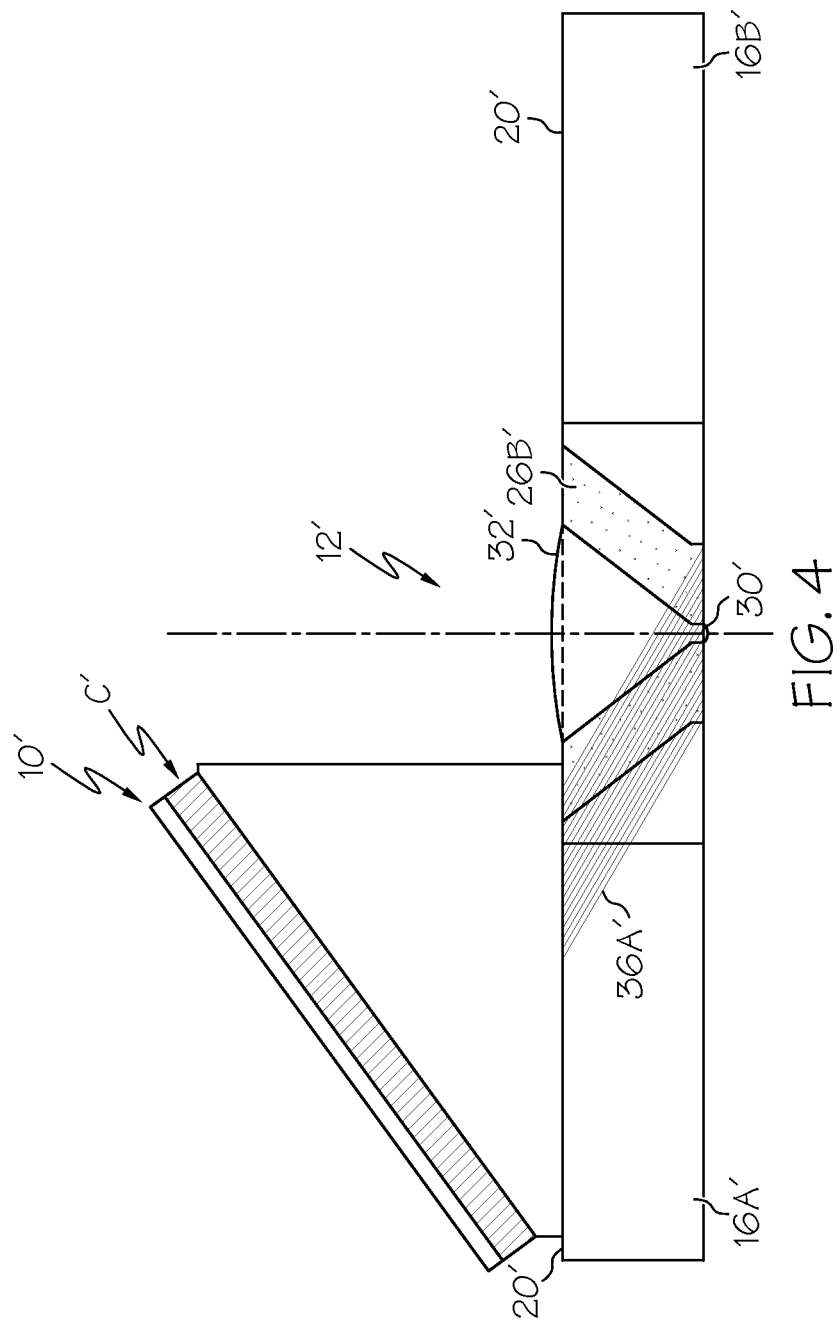

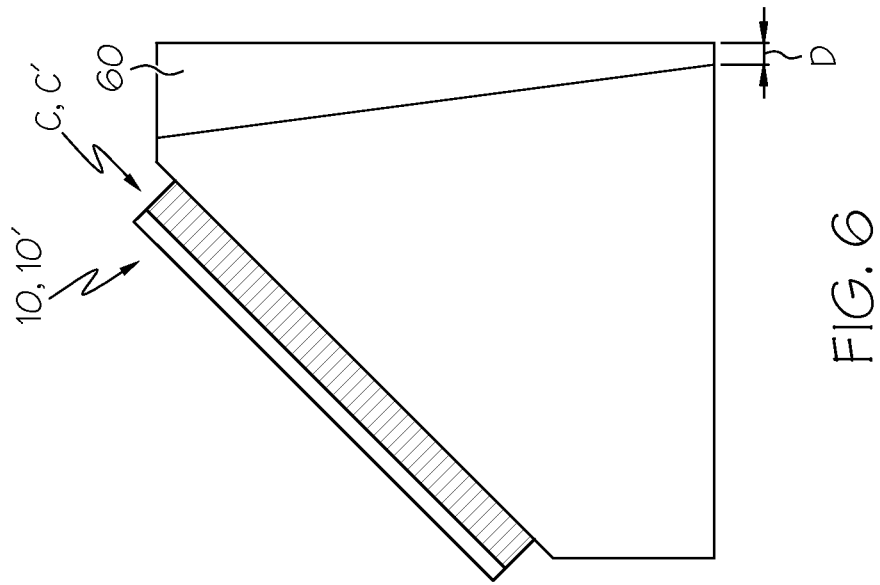
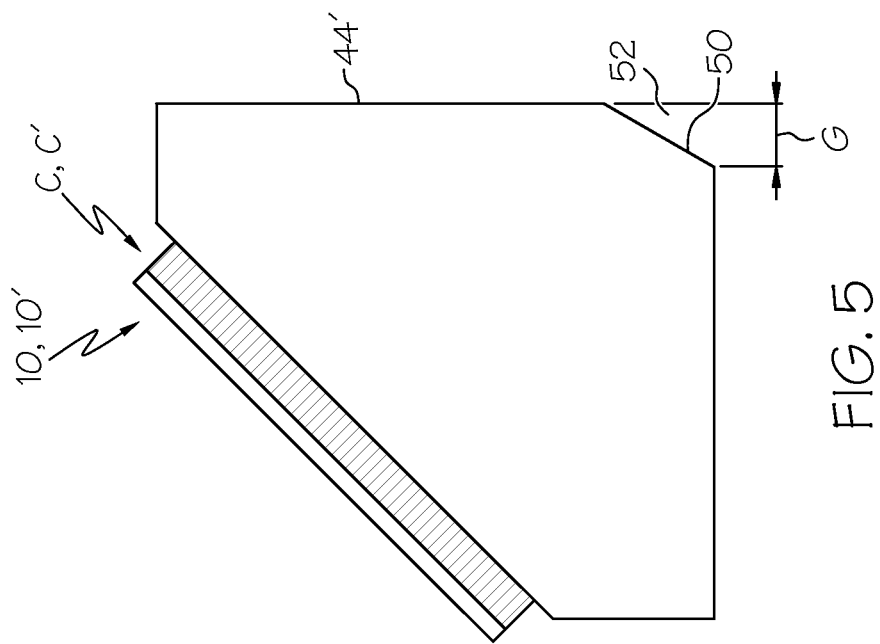

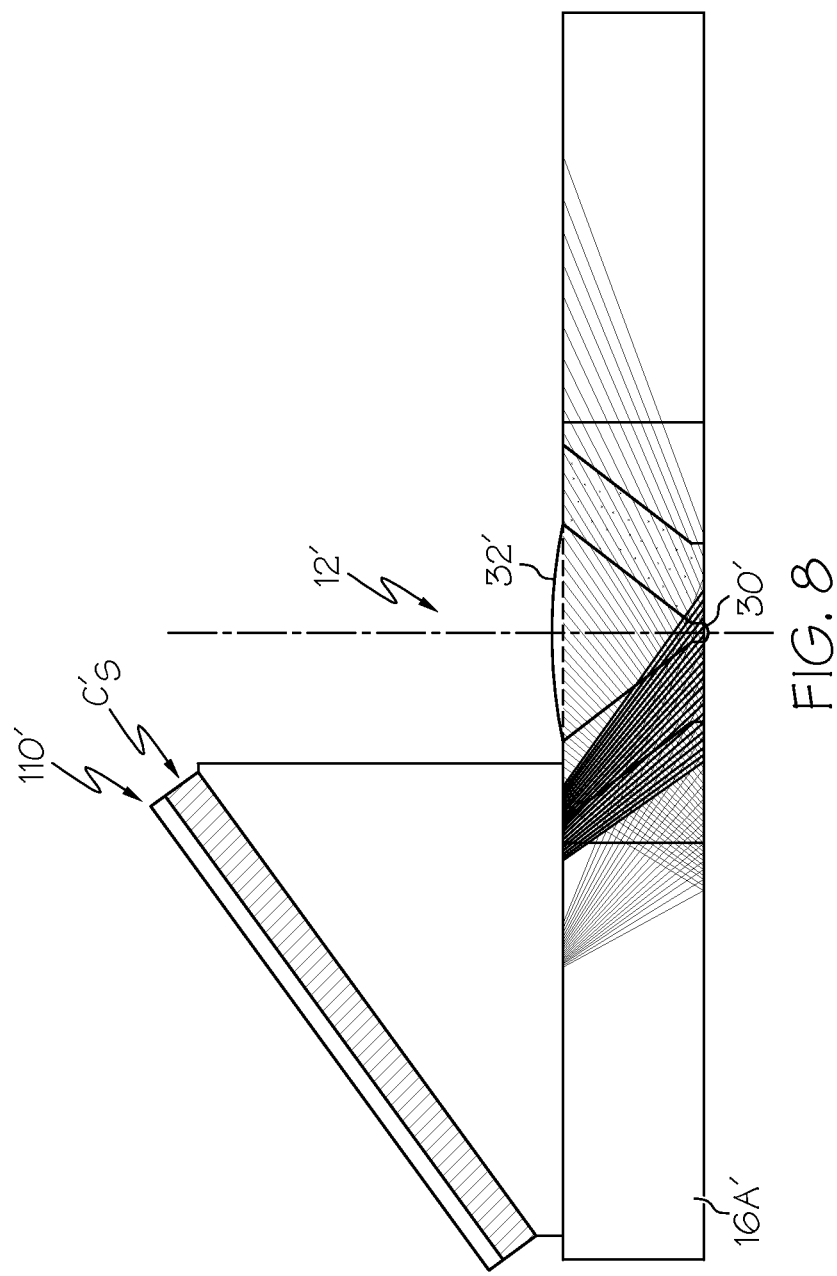

AUTO BEAM OPTIMIZATION FOR PHASED ARRAY WELD INSPECTION

BACKGROUND OF THE INVENTION

1. Field of Invention

The present invention relates to ultrasonic inspection of welds, and specifically relates to improved efficiency for completing inspection with an ultrasonic probe having an array of multiple ultrasonic elements.

2. Discussion of Prior Art

Ultrasonic probes are often used to inspect a weld that connects two portions (e.g., sheet members or pipe/conduit sections). Each ultrasonic probe can include a plurality of transducer elements. Each transducer element is capable of emitting a signal that proceeds though the one of the connected portions and into the weld itself. The probe includes a wedge so that the plurality of transducer elements are arranged in an array along the wedge, with each element being at a different location. The difference of location of each transducer element within the array extending along the wedge provides for an associated difference of possible area to which each transducer element will direct its respective signal.

Operation of a probe in order to inspect a weld is often referred to as a scan. In order to perform a scan, the probe is placed upon one of the connected portions at a moderate distance from the weld. The probe is operated (e.g., transducer signals emitted) and the probe is moved along the connected portion relative to the weld.

In order to accomplish useful inspection of a weld, it is common to perform at least two scans on each side of weld. Specifically, two scans on each side help provide for effective scan coverage of the weld. Both a root of the weld and a cap of the weld should receive effective scanning.

As mentioned, different transducer elements within the array can provide for different area sensing. As such, it is certainly possible that one or more transducer elements can be used to accomplish scanning of the weld root and one or more, different transducer elements can be used to accomplish scanning of the weld cap. In general, the weld root and the weld cap are in an area of interest to be scanned. However, it is possible that one or more of the transducer elements are not usable/needed to accomplish scanning of either the weld root or the weld cap (e.g., not within the area of interest). For example, it is possible for one or more certain beams not to pass through either the weld root area or the weld cap area. Perhaps the beams do not even pass near to either the weld root area or the weld cap area (e.g., not within the area of interest).

Turning briefly to FIG. 1, a previously known (e.g., prior) method/approach of operating all of the transducer elements of a linear is schematically shown via FIG. 1. If the particular task is to investigate/analyze a weld root 30', it can be appreciated that some (e.g., a majority in this case) of the transducer beams 36' will not provide useful data. Turning briefly to FIG. 2, another previously known (e.g., prior) method/approach of operating the transducer elements is schematically shown via FIG. 2. FIG. 2 presents an example of a sector-type probe 110' with multiple beams from two transducer elements simultaneously presented. It should be noted that the particular transducer elements/beams do not provide for efficient/effective coverage of the weld area. For example, it should be noted that a large portion of the beams do not enter an Area of Interest in a useful manner.

It is to be appreciated that operation of each transducer element requires a least some amount of energy and time. In addition, it is to be appreciated that processing of data obtained as a result of operation of each transducer element requires a least some amount of energy and time. As such, increased efficiency or energy and/or time can be obtained via operation of less than all of the transducer elements. However, it should further be appreciated that proper analysis requires that the one or more transducer elements needed to accomplish scanning of the weld root and the one or more, different transducer elements needed to accomplish scanning of the weld cap should of course be operated. As such, the inventors have determined that there is a need to both improve efficiency, via avoiding unnecessarily transducer element operation/data processing, and to accomplish proper analysis.

BRIEF DESCRIPTION OF THE INVENTION

The following summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

In accordance with an aspect, the present invention provides a method of computing optimal beam numbers of elements of a phased-array ultrasonic weld inspection arrangement. The arrangement is for inspecting a weld that is within an area of interest that has a known dimension and with the inspection arrangement being at a known offset distance from the weld. The selection is such that operation of the at least one element provides sufficient information data for weld analysis. The elements extend along an ultrasonic transmission wedge of the arrangement that supports the extent of the elements at a wedge angle relative to the welded material. The method includes utilizing the dimension of the weld area of interest and dimension of offset of the inspection arrangement from the weld within calculation that yields the selection of the at least one element.

BRIEF DESCRIPTION OF THE DRAWINGS

The foregoing and other aspects of the invention will become apparent to those skilled in the art to which the invention relates upon reading the following description with reference to the accompanying drawings, in which:

FIG. 4 is a schematic illustration similar to FIG. 1, but shows an approach of operating only transducer elements than necessary to obtain analysis of the root portion of the weld within the area of interest for efficiency;

FIG. 5 is a schematic illustration of a modified wedge usable within the probe of FIG. 3;

FIG. 6 is a schematic illustration of another modified wedge usable within the probe of FIG. 3;

FIG. 8 is a schematic illustration similar to FIG. 2, but shows an approach of operating only transducer elements than necessary to obtain analysis of the root portion of the weld and a cap portion of the weld within an area of interest.

DETAILED DESCRIPTION OF THE INVENTION

Figure 1:
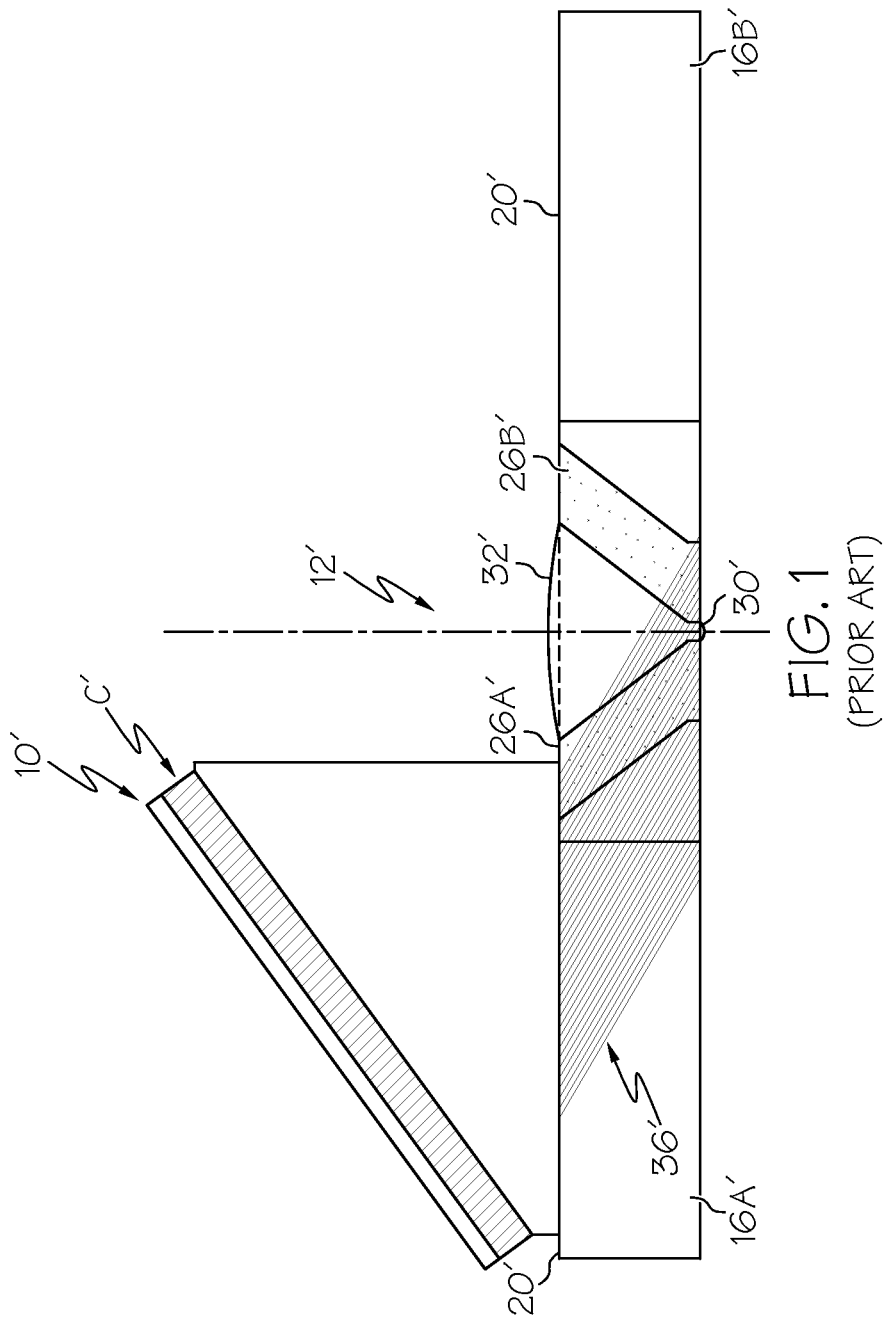
FIG. 1 is a schematic illustration that shows a prior art approach of operating more transducer elements than necessary to obtain analysis of a root portion of a weld within an area of interest.

Illustrative embodiments that incorporate one or more aspects of the invention are described and illustrated in the drawings. These illustrated examples are not intended to be overall limitations on the invention. For example, one or more aspects of the invention can be utilized in other embodiments. Moreover, certain terminology is used herein for convenience only and is not to be taken as a limitation on the invention. Still further, in the drawings, the same reference numerals are employed for designating the same elements.

An ultrasonic probe 10 is used to inspect an example weld 12 that connects two example portions 16A, 16B of material. It is to be appreciated that the connected portions 16A, 16B need not be a specific limitation upon the present invention. As such, the connected portions can be varied. Some examples of connected portions include sheet members or pipe/conduit sections. The two connected portions 16A, 16B of material can also be varied. Typical examples of the material of the connected portions 16A, 16B include various metals and may include ferrous-based metals, aluminum-based material, or the like. Each connected portion (e.g., 16A, 16B) includes a proximal (e.g., upper as viewed in the Figures) surface 20 and a distal (e.g., lower as viewed in the Figures) surface 22. In the shown example, the two connected portions 16A, 16B, and thus the surfaces 20, 22 are planar. However, it is to be appreciated that some curvature may be present.

The weld 12 that connects the two connected portions 16A, 16B fixes the two portions together and has been previously been completed (i.e., the weld is solidified). The weld 12 may have varied characteristics that need not be specific limitations upon the present invention. For example, the weld 12 may have varied shape and material characteristics concerning composite material(s). The composite materials may be dependent upon the material of the connected portions 16A, 16B. As such, the weld material may include a metal composition, including a ferrous-based or aluminum-based materials or the like.

The weld 12 extends along adjacent edges 24A, 24B of the connected portions 16A, 16B. Within the Figures, the weld 12 extends transverse (e.g., perpendicular) into and out of the plane of the drawing sheet. As such, the Figures show the weld 12 in cross-section. Thus, the weld 12 has a length (i.e., extends perpendicular away from the plane of the drawing sheet) and can be termed to be a weld line. During the creation process (i.e., the welding process) of the example weld 12 shown within the Figures, weld material is deposited. In addition, some of the material 26A, 26B of the connected portions 16A, 16B is altered by the application of heat during the weld creation process. Such altering may include melt or partial melt. This area can be referred to as the heat-affected area. As such, the example weld includes a weld root 30 located adjacent to the distal side 22 of the connected portions 16A, 16B and a weld cap 32 located adjacent to the proximal side 20 of the connected portions.

It should be noted that the connected portions 16A, 16B and the weld 12, as they appear within the drawings, are in cross-section. However, it should further be noted that the typical cross-section hatching of the connected portions 16A, 16B and the weld 12 are omitted for clarity since numerous lines representing beams, paths, dimensions, etc. (described below) are shown within the drawings to illustrate aspects of the invention.

It is typical that welds (e.g., weld 12) have an acceptable level of structural integrity and the like. As such, in accordance with one aspect of the present invention, the ultrasonic probe 10 is used to inspect the weld 12. Specifically, in the shown example, the probe 10 is operated during inspection of the weld 12 as the probe is moved relative to the weld (i.e., at a spaced distance from the weld line and substantially parallel to the weld line direction). Such operation is often referred to as a scan. In order to perform a scan, the probe 10 is placed upon one (e.g., 16A) of the connected portions 16A, 16B at a moderate distance from the weld 12. The probe 10 is operated and the probe is moved parallel to the connected portion relative to the weld 12.

In order to accomplish useful inspection of a weld 12, it is common to perform at least two scans, one on each side of weld 12. Specifically, two scans on the two sides help provide for effective scan coverage of the weld 12.

Turning to the details of the probe 10, the ultrasonic probe includes a plurality of ultrasonic transducer elements C in a linear matrix array. It is to be appreciated that FIG. 3 simply shows an example number of transducer elements C to convey the concept of a plurality of elements C and the shown number is not to be construed as a limitation. In addition, the specific details of the plurality of transducer elements C may be varied. For example, the plurality of transducer elements C may be appropriately connected to a power source, connected to data processing components, etc. Also, the physical construction concerning the transducer elements (e.g., extent/ spacing of the plurality of transducer elements) can be varied and thus need not be specific limitations upon the present invention.

Figure 3:
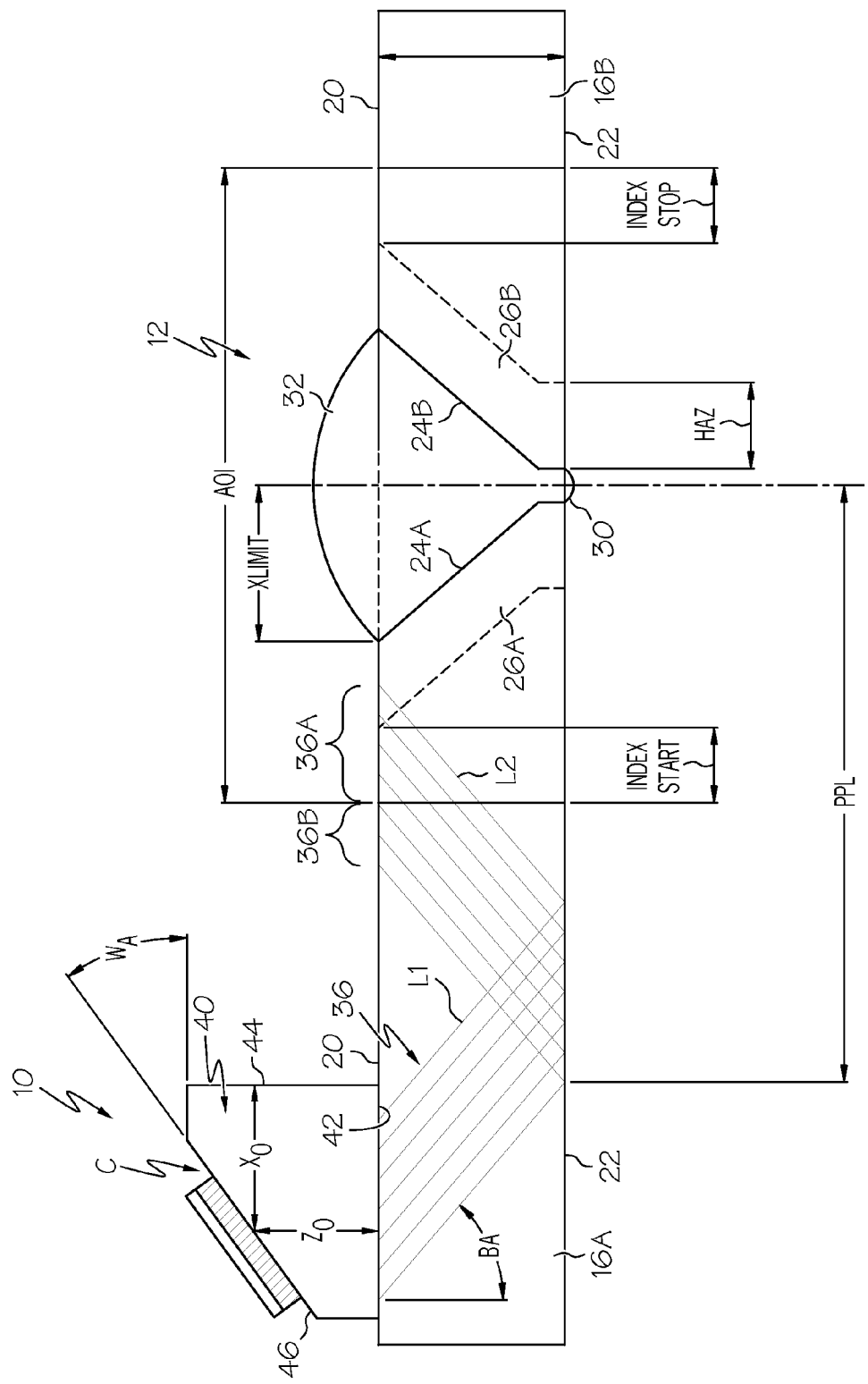
FIG. 3 is a schematic illustration of an example ultrasonic probe located upon two portions of material connected by a weld and shows the emittance of signals into a connected portion/weld, with selection of at least one element for selective signal emittance being able to improve efficiency in accordance with an aspect of the present invention.

Each transducer element C is capable of emitting an ultrasonic signal (e.g., an ultrasonic beam) 36 (several example beams in are shown in FIG. 3, which are not intended to present a limitation upon the present invention) that can proceed though the material of the connected portions 16A, 16B and the material of the weld 12. The signal can be reflected (echoed) back toward the transducer elements of the probe by various surface interfaces and by characteristic of the weld including defects (e.g., imperfections, deformities, voids, impurities, and the like) that provide surface interfaces.

The reflected signals can be analyzed in order to make determinations about the weld. The reflected signal data analysis can be accomplished via various techniques and as such the analysis need not be a specific limitation upon the present invention. Operation of such a probe 10, including the powering/operation of transducer elements C, and processing of signals/data derived from the transducer elements are known and can be varied. In addition, various components/ devices can be operatively connected to the probe to receive/ process the signals/data derived from the transducer elements to determine various characteristics of the weld including defects (e.g., imperfections, deformities, voids, impurities, and the like). Such components/devices and such reception/ processing are known and can be varied. Accordingly, such specifics need not be limitations upon the present invention.

Turning to the specific structure of the example probe 10, the ultrasonic transducer elements C are arranged in a linear array. As a reference, the linear array extends transverse (e.g., perpendicular) to the extent of the weld 12. Recall that the weld 12 extends perpendicular to the plane of the drawing sheet (e.g., into and out from the sheet). As such, the linear array extends within in the plane of the drawing sheet.

The probe 10 includes a wedge 40. The wedge 40 is made of ultrasonic transmissive material. The wedge 40 has a first side 42 for placement against the proximate surface 20 of one of the connected portions (e.g., 16A). As mentioned, the shown example connected portions (16A, 16B) are flat and as such the first side 42 of the wedge 40 has a complementary substantially flat face to mate against the flat of the connected portion 16A. A different contour of the connected portions can be accommodated via a complementary contour at the first side 42. A second side 44 in the shown example is perpendicular to the first side 42 and is also substantially flat. However it is contemplated that a different configuration is possible. A third side 46 can be referred to as a hypotenuse side and extends at an angle to the first side 42 and thus the flat of the connected portion (e.g., 16A). The hypotenuse side extends at a wedge angle $W_A$. It is contemplated that the hypotenuse side 46 need not extend completely to the first and second sides 42, 44 and the shown example presents truncations so that the hypotenuse side 46 does not extend completely to the first and second sides.

The array of transducer elements C is located on the hypotenuse side 46 of the wedge 40 such that the array extends vertically up at an angle and away from the connected portion (e.g., 16A) as the array laterally extends toward the weld 12. As such, the plurality of transducer elements C are arranged in the array along the wedge 40, with each element being at a different location. The difference of location of each transducer element C within the array extending along the wedge 40 provides for an associated difference of possible area to which each transducer element will direct its respective signal (see for example FIG. 3). Specifically, each of the transducer elements C within the array emits a respective signal that enters the wedge at a different location and thus enters the connected portion (e.g., 16A) at a different location. As mentioned, some example beam 36 from different transducer elements C are shown within the connected portion 16A and the weld 12 in FIG. 3. It is to be appreciated that the beams traveling through the wedge 40 are not shown in FIG. 3 for clarity and also some of the overall possible beams may not be shown. It should be noted that the plural beams (FIG. 3) within the presented example are directed so at to proceed parallel to each other as they proceed from the array of transducer elements C.

Turning back to the aspect of each beam entering the wedge at a different location and thus entering the connected portion (e.g., 16A) at a different location, such difference provides for different transducer elements beams 36 to be able to "sense" (e.g., investigate, interrogate, etc.) a different location, including possibly different locations that may or may not contain the weld and specifically to different locations that may contain different portions of the weld. An ability to effectively and efficiently scan and analyze all portions of the weld (i.e., including the weld root 30 and the weld cap 32) is beneficial. So logically, different transducer elements C and associated different beams 36 can be employed to accomplish this beneficial function. It should also be noted that merely utilizing all transducer elements/beams is somewhat inefficient since some beams will not travel through any portion of the weld area at all and thus do not have an ability to detect/provide information about the weld/weld area.

In general, the area that needs to be investigated/analyzed is the weld itself and at least some minimum surrounding area which includes the heat-affected areas (e.g., melt/partial melt) of the connected portions 16A, 16B. As a corollary, at least some, and likely most (e.g., a bulk), of the connected portions 16A, 16B need not be investigated/analyzed. The area that needs to be investigated/analyzed (i.e., the weld and some surrounding area) is referred to as the Area of Interest (identified as AOI within FIG. 3). The size of the Area of Interest that needs to be investigated/analyzed can be dependent upon several factors such as weld size, weld type, thickness of the connected portions 16A, 16B.

Operating/utilizing only some of the transducer elements C to provide the needed investigation/analysis of such an area provides efficiencies, such as cost efficiencies and time efficiencies. Specifically, operation of transducer elements C and processing of data from transducer elements requires both energy and time. A reduction of the number of transducer elements C operated and/or amount/volume of data processed provides savings. However, it should be appreciated that a minimum, and correctly located, amount of transducer elements C should be operated, and data therefrom processed, to effectively scan the weld.

Focusing again upon FIG. 3, it should be noted that within the shown example, only some beams 36 from the transducer elements C are shown. It is to be appreciated that the shown transducer beams 36 need not be all of the possible transducer beams that may be output from the array of transducer elements C. The shown transducer beams 36 are simply a representative portion to help illustrate an aspect of the present invention.

The shown transducer beams 36 proceed within the connected portion (e.g., 16A) along two legs L1, L2 (with each leg extending between the surfaces 20, 22 and terminating at reflection). However, a first sub-set of the transducer beams 36A proceeds into the area of interest (AOI), while a second subset of beams 36B does not so proceed into the area of interest. The first subset of beams 36A will likely provide useful data concerning weld investigation/analysis, whereas the second subset of beams 36B will likely not provide useful data concerning weld investigation/analysis. Thus, in accordance with an aspect of the present invention, the beams of the second subset 36B can be segregated out so that the associated transducer elements are not so operated and/or data that would be associated with the beams of the second subset would not be processed. This, segregation to reduce or lower the amount of transducer element operation and/or associated data analysis is easily appreciated via a comparison of FIGS. 2 and 3.

Turning to a comparison of FIGS. 1 and 4, it is to be appreciated that similar reference numerals are used to represent similar structures/features, but with a prime (') added in FIG. 1. Before proceeding to further discussion about FIGS. 1 and 4, it should be appreciated that, as compared to FIG. 3, FIGS. 1 and 4 also show a slightly different probe 10', slightly different connected portions and weld 16A', 16B', 12' and a slightly different relative positioning of the probe to the weld. These slight variations are to emphasize that difference are possible.

Proceeding now with the comparison, recall that the previous approach shown FIG. 1 presents the aspect that some (e.g., a majority in this case) of the transducer beams 36' will not provide useful data. In distinction, turning to FIG. 4, a group (identified as 36A') selected in accordance with an aspect of the present invention provides useful data about the weld root 30'. The present invention includes the aspect of calculating the number of beams that will proceed to a particular area (e.g., the area of interest or a specific portion of the area of interest). As a corollary, the present invention includes the aspect of calculating the number of beams that will not proceed to the particular area (e.g., the area of interest or a specific portion of the area of interest).

The calculation can take into account many features and variables of the probe (e.g., 10 or 10') being utilized. For example, the probe may have a wedge that includes a "clipped" leading edge 50 (see FIG. 5). Specifically, a corner of the wedge that is adjacent to the surface 20 and closest to the weld 12 is removed to provide for an open or "clipped-away" area 52. Such a clipped leading edge 50 can provide for position of the probe at a relatively close proximity to the weld (e.g., immediately adjacent) while avoiding adverse contact with raised portions (e.g., the weld crown). However, such a clipped leading edge 50 does provide a front gap has a horizontal distance G through which transducer beams do not travel. As another possible example feature, the transducer may have a wedge that include a front material segment 60 made of a different material that damps ultrasonic beams from proceeding there through. See FIG. 6. Such a material segment 60 can be used for controlling ultrasound beam reflection. Such a front material segment 60 can have a distance D.

Figure 7:
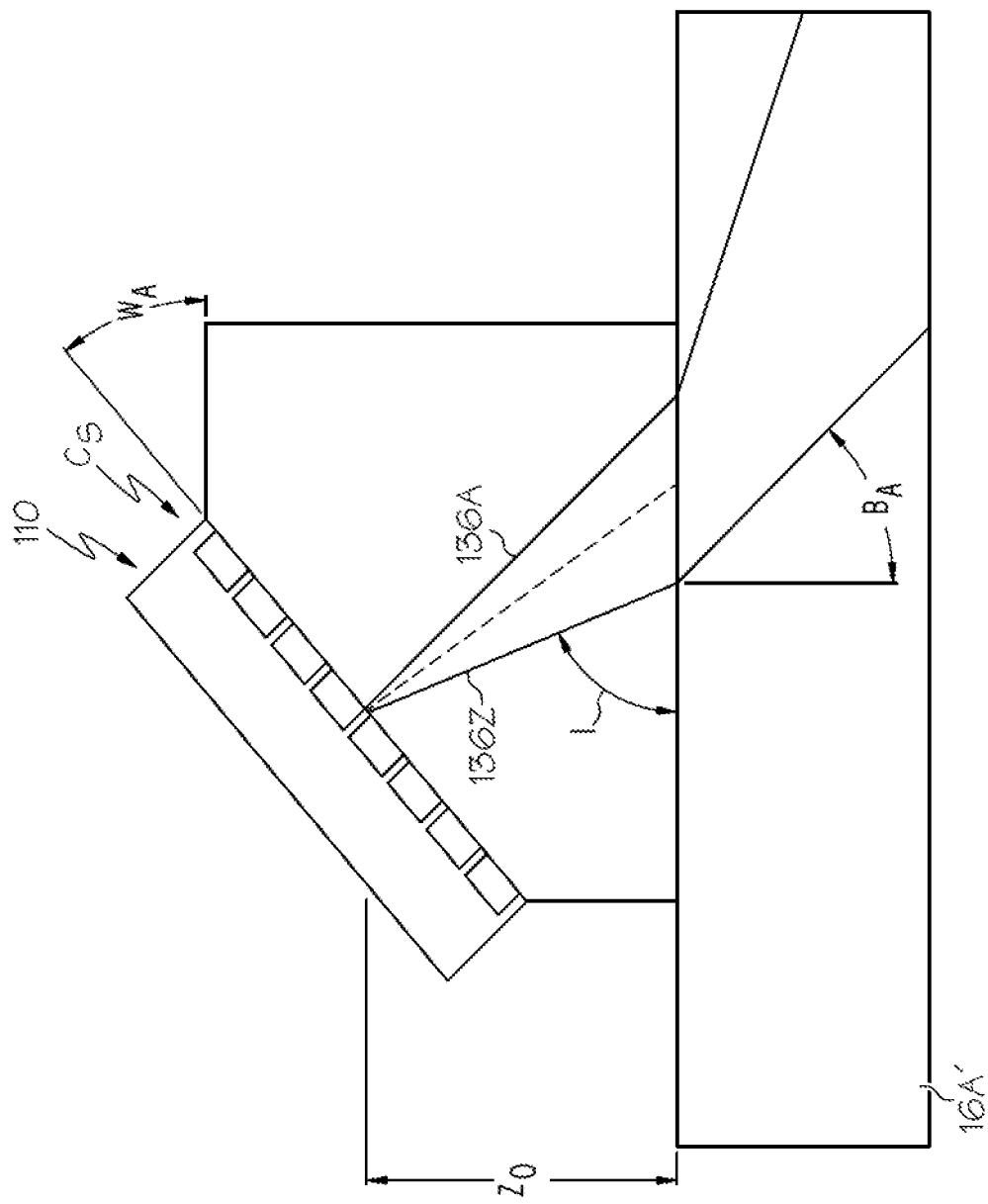
FIG. 7 is a schematic illustration showing another example ultrasonic probe located upon a portion of material connected by a weld, with the probe providing sectorial scanning.

As still further features of the probe that can be taken into account in order to determine/select the sub-set group transducer elements/associated beams to accomplish the investigation/analysis, the probe may be a scanning-type probe 110 (FIG. 7). The scanning-type probe can also be referred to as a sector-type. FIG. 7 shows an example range within which a particular sector-type transducer element $C_s$ can direct its beam. Specifically with FIG. 7, the dash line proceeding from the particular transducer element $C_s$ indicated a normal (i.e., perpendicular) direction from transducer element. The beam path indicated by reference numeral 136A indicates a first example beam path along a furthest reach of the scan. The beam path indicated by 136Z indicates an example last beam path along a furthest reach of the scan. As can be appreciated, the two furthest reaching beam paths 136A, 136Z have different entry points into the connected portion 16A and that as the beam moves or scans between these two furthest reaching beam paths, 136A, 136Z, the beam will have an ever-changing path. In addition, as can be appreciated upon viewing FIG. 7, the path of the beam through the connected portion 16A will thus vary. Still further, similar variations of beam paths will occur for the other beams from the other transducer elements of the sector-type probe 110.

Figure 2:
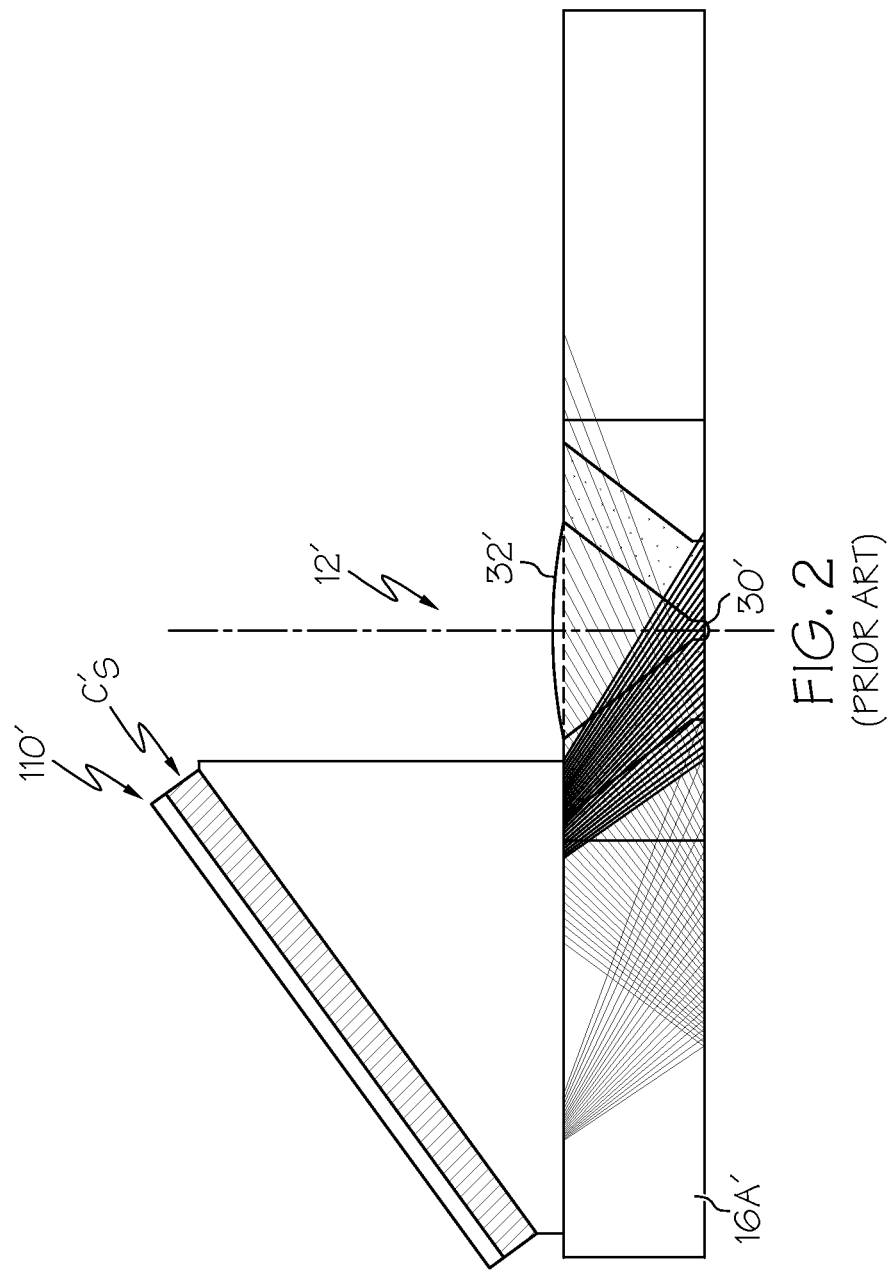
FIG. 2 is another schematic illustration that shows another prior art approach of operating more transducer elements than necessary to obtain analysis of a root portion of the weld and a cap portion of the weld within an area of interest.

Turning to a comparison of FIGS. 2 and 8, it is to be appreciated that similar reference numerals are used to represent similar structures/features, but with a prime (') added in FIG. 2. Within FIG. 2, the particular transducer elements/beams do not provide for efficient/effective coverage of the weld area. For example, it should be noted that a large portion of the beams do not enter the Area of Interest in a useful manner. FIG. 8 provides an example in accordance with an aspect of the present invention and presents beams from two transducer elements that efficient/effective coverage of the weld area. Note that the beams of one transducer element are efficiently/effectively providing coverage for the weld root 30' and that the beams from another transducer element are efficiently/effectively providing coverage for the weld cap 32'.

As mentioned, different transducer elements can provide for different area sensing. As such, in accordance with an aspect of the present invention, it possible that one transducer element, or smaller group of transducer elements, can be used to accomplish scanning of the weld root and another transducer element, or smaller group of transducer elements, can be used to accomplish scanning of the weld cap. As another aspect of increased efficiency the other/remaining transducer elements that may not provide for desired scanning can idled or otherwise omitted from operation. However, because it may not be initially known which transducer element(s) will properly accomplish thus an aspect of the present invention is to make determinations of such.

Selection of transducer elements of the array to utilize/not utilize is provided by a process in accordance with the present invention. One example series of algorithms is provided to do such a process. It is to be appreciated that other algorithms are possible and are to be considered to be within the scope of the present invention.

In general, it is to be appreciated that one example process is presented herein. It is to be appreciated that the process may be varied and that other, different processes can also be utilized. It is to be appreciated that such variations and differences are contemplated to be within the scope of the present invention. As such, the present example is not to be considered a limitation boundary of the present invention. For ease of understanding the following nomenclature is presented. It is to be appreciated that the nomenclature can also be varied without departing from the present invention.

Nomenclature:
N0=Total number of transducer elements within the array of the probe
Part Entry Point=(For sector type only) Is the entry point at the furthest beam
Nominal Point=(For sector type only) Is the point at which the beam will enter the connected portion as it would proceed in a nominal (e.g., perpendicular to transducer element array)
I=incidence angle
WA=Wedge angle, which is the angle between the upper surface of the connected portion (i.e., the be welded portion) and the array of transducers as defined by the wedge interposed there between
BA=Beam Angle as the beam enters the connected portion
$Z_0$=Vertical wedge offset, which is the vertical distance of the Probe element from the welded material
$X_0$=Horizontal wedge offset, which is the horizontal distance of the center element from the edge of the wedge closest to the weld
VW=Wedge Velocity, which is the known velocity of the ultrasonic beam within the wedge
VS=Material Velocity, which is the known velocity of the ultrasonic beam within the material of the connected portion
TZ=Material Thickness, which is the vertical thickness of the connected portion that is welded
Leg=Number of times beam bounce/reflect inside the connected portions
Pitch=Center to center distance between two adjacent probe elements
HAZ=Parent metal, horizontal width of heat affected zone on parent metal. That is heat transferred from molten metal on weld preparation
XLIMIT=one half of the width of the weld cap (Overcap-Width/2)
PPL=ProbePositionLeft, is the horizontal offset from a weld centerline to the edge of the wedge
INDEXSTART=is the horizontal dimension from the outer edge of the HAZ (Disturbed parent metal) to the edge of the Area of Interest (AOI) at the near side of the weld
INDEXSTOP=is the horizontal dimension from the outer edge of the HAZ (Disturbed parent metal) to the edge of the Area of Interest (AOI) at the far side of the weld
Steps of the example process:
Beam Coordinates Calculation
This calculation is to derive the values of probe exit point and part entry point in terms of horizontal and depth axes. The coordinates will vary for each beam based on its angle of refraction. Hence the given below formula for any beam angle. Substitute the appropriate beam angle and other parameters to get the correct value.

Part Entry Point Calculation:
  Part Entry Point Depth=0 mm
  Part Entry Point Horizontal has to be computed in four steps.

Step 1: Calculation of Nominal Entry Point $$\text{Nominal Point in } mm = Z_0 * \text{Tan}(W_A)$$

Step 2: Calculation on incidence angle (I)

$$\text{Incidence Angle (in degrees)} = \arcsin[\sin(\text{Highest Beam Angle}) * (V_W/V_S)]$$

Step 3: Calculation of Beam Entry Point $$\text{Beam Entry Point in } mm = Z_0 * \text{Tan (Incidence Angle)}$$

Step 4: Calculation of Part Entry Point Horizontal

Part Entry Point Horizontal=Beam Entry Point−Nominal Point

Probe Exit Point Calculation

Probe Exit Point Depth=−[Wedge Offset Z]

Probe Exit Point Horizontal=−[(Wedge Offset Z)*tan (Wedge Angle))]

Beam coordinates are based upon the Part Entry Point Depth and the Part Entry Point Horizontal.

It is to be appreciated that the above calculations is specific to sector-type and linear scan-type need not utilize all of the above calculations. The overall calculation process can thus proceed, with an understanding that dependent upon scan type, etc. some parameter/calculation steps are moot.

Thus proceeding with the calculation:
clsPass.StartAngle=clsPass.SectorScanAngleStart (which is used to set an angle value);
IList<BeamCoordinates>beamCoordinates=Beam Coordinates.GetBeamCoordinates(clsPass, $X_0$, $W_A$, BA, $V_w$, $T_Z$, $N_0$, Pitch);
int noOfBeamsOutOfAOI=0 (the process is initiated with a presumption that none of the beams are outside of the Area of Interest);
double BA=0;
for int i=0; i<beamCoordinates.Count; i++(for sequencing through the various available beams, either just a linear array sequence or with the angle steps of associated with sectorial scanning)
if clsPass.PassDefinitionMethod=PassDefinitionMethod. MultipleSectorialScans (for sectorial scanning)
  if (i=0), then BA=clsPass.SectorScanAngleStart
  else, BA=BA+clsPass.SectorScanAngleStep
else if clsPass.PassDefinitionMethod=PassDefinitionMethod. MultipleLinearScans (for linear scanning)
  BA=clsPass.LinearScanBeamAngle
if clsPass.PassType=InspectionPassType.Left_Cap||clsPass. PassType=InspectionPassType.Left_LowerCap||clsPass. PassType=InspectionPassType.Left_Root||clsPass.Pass Type=InspectionPassType.Left_Single (for a pass that is from the left for any of the weld types)

double Length1=*cls*Pass.*PPL*+$X_0$−INDEXSTART−*XLIMIT*−*HAZ*−$Z_0$*TanOfDegrees(*WA*) (a calculation for Length 1)

double Length2=*cls*Pass.Leg*$T_z$*TanOfDegrees(*BA*)+ beamCoordinates[*i*].PartEntryPointHorizontal (a calculation for Length 2)

if (Length2<Length1), then Beam is of AOF, add to noOfBeamsOutOfAOF else if (clsPass.PassType=InspectionPassType.Right_Cap||clsPass.PassType=InspectionPassType.Right_Lower Cap||clsPass.PassType=InspectionPassType.Right_Root||clsPass.PassType=InspectionPassType.Right_Single (for a pass that is from the left for any of the weld types)

double Length1=*cls*Pass.ProbePositionRight+ Wedge.Offset*X*−INDEXSTOP−*XLIMIT*−*HAZ*−$Z_0$*TanOfDegrees(*WA*) (a calculation for Length 1)

double Length2=*cls*Pass.Leg*$T_z$*TanOfDegrees(*BA*)+ beamCoordinates[*i*].PartEntryPointHorizontal (a calculation for Length 2)

if (Length2<Length1), then Beam is of AOI, add to noOfBeamsOutOfAOI;
return noOfBeamsOutOfAOI (which returns an indication of the number of beams that are outside of the area of interest and thus indicates the transducer elements for which operation can be omitted for efficiency).

Thus, the technical effect is to provide a method of determining the transducer elements for which operation can be omitted for efficiency. Examples of omitted operations include: (1) not operating some of the transducer elements so that beams are not even emitted and (2) not utilizing data obtained from some of the transducer elements. Omission of such operations provides savings in operation costs and operation time. It is to be appreciated that the process in accordance with to the present can be performed via the aid of a calculation device and/or a computer. Of course, in a most basic form, the process can be performed without the aid of such devices. However, use of such devices would itself provide for improved efficiency.

An example of the invention has been described with reference to the example embodiments described above. Modifications and alterations will occur to others upon a reading and understanding of this specification. Example embodiments incorporating one or more aspects of the invention are intended to include all such modifications and alterations insofar as they come within the scope of the appended claims.

What is claimed:

1. A method of computing optimal beam numbers of a phased-array ultrasonic weld inspection arrangement inspecting a weld that is within an area of interest that has a known dimension and with the inspection arrangement being at a known offset distance from the weld, such that operation of the at least one element provides sufficient information data for weld analysis, wherein the elements extend along an ultrasonic transmission wedge of the arrangement that supports the extent of the elements at a wedge angle relative to the welded material; the method including:
  utilizing the dimension of the weld area of interest and dimension of offset of the inspection arrangement from the weld within calculation that yields the selection of the at least one element.

2. A method as set forth within claim 1, wherein the calculation includes iterations of successive calculation steps, with each step determining whether a successive element should be included within the selection of the at least one element that provides sufficient information data for weld analysis.

3. A method as set forth within claim 1, wherein the selection of the at least one element includes selection of plural elements.

4. A method as set forth within claim 3, wherein the weld includes a weld root and a weld cap, the selection of the at least one element includes selection of at least one element that provides sufficient information data for weld root analysis and selection of at least one different element that provides sufficient information data for weld cap analysis.

5. A method as set forth within claim 1, wherein the method is utilized with an inspection arrangement that has an array of linear scan elements.

6. A method as set forth within claim 1, wherein the method is utilized with an inspection arrangement that has an array of sector scan element.

7. A method as set forth within claim 1, wherein the elements extend along an ultrasonic transmission wedge of the arrangement that supports the extent of the elements at a wedge angle relative to the welded material, and the method includes utilizing the wedge angle within the calculation that yields the selection of the at least one element.

8. A method as set forth within claim 1, wherein the calculation includes utilizing the dimension of a cap of the weld.

9. A method as set forth within claim 1, wherein the calculation includes utilizing the dimension of welded material that has been heat affected by the weld.

10. A method as set forth within claim 1, wherein the calculation includes utilizing an angle that the beam proceeds into welded material.

\* \* \* \* \*